United States Patent [19]
Sekiyama et al.

[11] Patent Number: 5,417,974
[45] Date of Patent: May 23, 1995

[54] BIOCIDAL SELF-ADHESIVE AND PROCESS FOR PRODUCING THE SAME, AS WELL AS SELF-ADHESIVE AND APPLICATION THEREOF

[75] Inventors: Yasushi Sekiyama, Nishinomiya; Yuichi Mizukami, Kobe; Shuzo Nakagawa, Soka; Hideaki Okabe; Kazuya Katoh, both of Urawa; Hiroshi Nagaki, Hiki, all of Japan

[73] Assignee: The Green Cross Corporation, Osaka, Japan

[21] Appl. No.: 934,453

[22] PCT Filed: Aug. 28, 1992

[86] PCT No.: PCT/JP92/01100

§ 371 Date: Sep. 14, 1992

§ 102(e) Date: Sep. 14, 1992

[87] PCT Pub. No.: WO93/09196

PCT Pub. Date: May 13, 1993

[30] Foreign Application Priority Data

Nov. 8, 1991 [JP] Japan ................. 3-100116 U
Nov. 8, 1991 [JP] Japan ................. 3-321003
Nov. 8, 1991 [JP] Japan ................. 3-321005

[51] Int. Cl.⁶ .................................. A01N 25/34
[52] U.S. Cl. ........................ 424/411; 424/405; 424/407; 424/412; 424/413; 428/411.1
[58] Field of Search ........... 428/343, 355, 480, 411.1; 424/448, 449, 447, 404, 411, 412, 413, 405, 407

[56] References Cited

U.S. PATENT DOCUMENTS

| | | | |
|---|---|---|---|
| 3,864,468 | 2/1975 | Hyman et al. | 424/404 X |
| 4,021,595 | 5/1977 | Kiritani et al. | 428/905 X |
| 4,451,568 | 5/1984 | Schneider et al. | 428/420 X |
| 4,830,860 | 5/1989 | Ranade | 424/411 X |
| 4,921,702 | 5/1990 | Banks et al. | 424/404 |
| 5,045,601 | 9/1991 | Capelli et al. | 428/343 X |
| 5,130,139 | 7/1992 | Cormier et al. | 428/448 X |
| 5,196,202 | 3/1993 | Konishi | 424/448 |
| 5,225,199 | 7/1993 | Hidaka et al. | 428/448 X |
| 5,236,713 | 8/1993 | Wato et al. | 424/448 X |
| 5,252,542 | 10/1993 | Allan | 424/413 X |

FOREIGN PATENT DOCUMENTS

| | | |
|---|---|---|
| 57-130989 | 8/1982 | Japan . |
| 62-48764 | 3/1987 | Japan . |
| 62-158672 | 7/1987 | Japan . |
| 2-109962 | 4/1990 | Japan . |
| 2-113876 | 4/1990 | Japan . |
| 2-273603 | 11/1990 | Japan . |
| 3-2235 | 1/1991 | Japan . |
| 3-151972 | 6/1991 | Japan . |

Primary Examiner—Daniel R. Zirker
Attorney, Agent, or Firm—Armstrong, Westerman, Hattori, McLeland & Naughton

[57] ABSTRACT

A self-adhesive article which is produced by forming an adhesive layer from an adhesive consisting essentially of a polymer which is soluble in or swellable by an iso-thiocyanate, impregnating the adhesive layer with an iso-thiocyanate to provide a biocidal self-adhesive, and applying the biocidal self-adhesive to at least one surface of a base material. A high concentration of the iso-thiocyanate can be held in the adhesive layer, and the self-adhesive article is put to uses intended for the purpose of providing bactericidal, fungicidal and microbiocidal effects in building and food-related fields and the like.

20 Claims, 3 Drawing Sheets 5,417,974

BIOCIDAL SELF-ADHESIVE AND PROCESS FOR PRODUCING THE SAME, AS WELL AS SELF-ADHESIVE AND APPLICATION THEREOF

TECHNICAL FIELD

The present invention relates to a biocidal self-adhesive comprising an adhesive containing an iso-thiocyanate efficiently held therein to have bacteriostatic, bactericidal and antimicrobial properties and the like, and a process for producing the same, as well as a self-adhesive article made by efficiently applying such a self-adhesive onto a support. Particularly, the present invention relates to such a biocidal self-adhesive which can be put to uses widely intended for the purpose of providing bactericidal, fungicidal and microbiocidal effects in building and food-related fields and the like.

The present invention also relates to an iso-thiocyanate gradually-releasing sheet, as an application of a self-adhesive article of the type described above, made by efficiently holding an iso-thiocyanate onto a support such as a paper, a non-woven fabric or the like through the medium of an adhesive or a low volatile oily liquid, so that the sheet has antibacterial, bactericidal and antimicrobial properties and the like, and particularly, such an Iso-thiocyanate gradually-releasing sheet which can be put to uses widely intended for the purpose of providing bactericidal, fungicidal and microbiocidal effects in various fields such as building, food-related and shoe insole fields.

Further, the present invention relates to a biocidal or freshness-maintaining self-adhesive sheet, as another application of a self-adhesive article of the type described above, having antibacterial and bactericidal properties and made by efficiently applying an adhesive containing an iso-thiocyanate held therein onto a support, and to a sterilizing and freshness-maintaining method using such a sheet for the purpose of providing bactericidal, fungicidal and microbiocidal effects to a variety of materials to be enclosed by the sheet, including food products such as vegetables and fruits, fresh foods, dried goods and grains.

BACKGROUND ART

It is known that an iso-thiocyanate contained in a mustard or a wasabi (i.e., Japanese horseradish) have bacteriostatic and bactericidal actions, and any of the synthetic and natural iso-thiocyanates provides bacteriostatic and bactericidal effects even at an extremely small concentration of vapor thereof on the order of 10-odd ppm to hundreds ppm. Before now, after reporting of this fact, several attempts have been made to adsorb the iso-thiocyanate to a porous carrier such as clay minerals or to a surface of a film or a sheet to industrially utilize the bacteriostatic and bactericidal actions thereof, and a certain article made in such a manner, e.g., a freshness maintaining material, has been brought o market.

In the above prior art, however, it is impossible to utilize the bacteriostatic and bactericidal actions of the iso-thiocyanate profitably. This is because much of the iso-thiocyanate adsorbed in these methods volatilizes off in the course of production of the article or during storage of the article, because of its high volatility, and consequently, an effective amount of iso-thiocyanate cannot be supported on a carrier. Particularly, when the iso-thiocyanate is adsorbed to a porous carrier, it is necessary to take a measure such that the iso-thiocyanate supported on a porous carrier is placed into a sack having a gradually releasing property, because the releasing rate largely depends upon the temperature. When the iso-thiocyanate is adsorbed to a film or a sheet, there is encountered a problem that it is difficult to impregnate the film or the sheet with an amount of iso-thiocyanate sufficient to exhibit an efficacy, but also it is difficult to control the gradual release.

The freshness maintaining means which has conventionally been used is a vacuum pack, or Ageless (Trademark) which is a deoxygenator consisting essentially of active iron oxide, for preventing the oxidation and the propagation of bacteria. However, with the vacuum pack, a special apparatus is required, and with the Ageless, it is necessary to pack the Ageless together with a material to be packed. Many food products such as breads, fishes, meats, box lunches, etc., are only packed with a film such as polyvinylidene chloride and polyethylene (PE) films, or only placed into a container made of a polyvinylidene chloride or a polyethylene. In this case, they are, of course, not durable at room temperature and hence, it is necessary to store them, for example, in a refrigerator.

Thereupon, it is conceived to utilize a freshness maintaining material made using the iso-thiocyanate, but this is also accompanied by the above-described problems, resulting in a difficulty to put it to practical use.

DISCLOSURE OF THE INVENTION

The present inventors have repeated zealous studies and as a result, it has been found that by using, as an adhesive, a polymer soluble in or swellable by an iso-thiocyanate, the iso-thiocyanate can be held in the polymer by impregnation, with physical properties of the adhesive being maintained, thus overcoming the above-described problems.

A biocidal self-adhesive according to the present invention comprises an adhesive impregnated with an iso-thiocyanate to hold the latter therein, the adhesive consisting essentially of a polymer which is soluble in or swellable by the iso-thiocyanate.

A process for producing a biocidal self-adhesive according to the present invention comprises the steps of forming an adhesive layer from an adhesive consisting essentially of a polymer which is soluble in or swellable by an iso-thiocyanate, and impregnating the adhesive layer with the iso-thiocyanate.

Further, a self-adhesive article according to the present invention is made by applying a biocidal self-adhesive of the type described above onto at least one surface of a base material.

Examples of the adhesives consisting essentially of the polymer soluble in or swellable by the iso-thiocyanate include acrylic adhesives such as copolymers of one or more of acrylic and methacrylic esters including n-butyl acrylate and methacrylate, hexyl acrylate and methacrylate, iso-octyl acrylate and methacrylate, 2-methoxyethyl acrylate and methacrylate, 2-ethylhexyl acrylate and methacrylate, decyl acrylate and methacrylate, dodecyl acrylate and methacrylate, tridecyl acrylate and methacrylate, with a functional monomer which is copolymerizable with such esters, such as acrylic, methacrylic, itaconic, maleic and anhydrous maleic acids, hydroxyethyl acrylate, hydroxypropyl acrylate, acrylic amido, dimethylacrylic amido, methylaminoethyl methacrylate, and methoxyethyl acrylate and methacrylate; vinyl polymer adhesives such as ethyl-vinyl ether, propyl-vinyl ether, butyl-vinyl ether and 2-ethylhexyl-vinyl ether; and rubber-based adhesives consisting essentially of natural rubbers and synthetic rubbers such as styrene-isoprene-styrene block terpolymer, styrene-butadiene copolymer, polybutene and butyl rubbers.

The acrylic, rubber-based and vinyl polymer adhesives can be selectively used, but it is preferred to selectively use any one of the acrylic adhesives. A particularly preferable adhesive is a copolymer of an alkyl acrylate or methacrylate having 4 or more carbon atoms in an alkyl group and a monomer which is copolymerizable with such ester monomer, and a cross-linked copolymer is more preferable.

Optionally, other additives may be incorporated into the adhesive, including tackifiers such as terpene and petroleum resins; softeners such as liquid paraffin, animal and vegetable oils, e.g., olive, soybean and bovine oils and lard, polybutene, lower isoprene and was; fillers such as titanium oxide, zinc oxide, aluminum metasilicate, calcium sulfate and calcium phosphate; water; emulsifiers such as sorbitan mono-oleate, sodium lauryl sulfonate, emulsifier aids such as magnesium and aluminum stearates. It should be noted that any of the adhesives other than those described herein can be used, if they are capable of being dissolved in an iso-thiocyanate or impregnated with an iso-thiocyanate by swelling to hold the iso-thiocyanate therein.

The iso-thiocyanates which can be used are various esters irrespective of aliphatic or aromatic type such as the allyl and alkyl esters of iso-thiocyanic acid, but particularly when the self-adhesive of the present invention is intended for food products, it is preferred to use natural iso-thiocyanate contained in an extract from a mustard and the like.

The adhesive is preferably impregnated with an iso-thiocyanate to hold the latter therein at a concentration within a range of 0.1 to 50% by weight based on the adhesive, and desirably to hold the iso-thiocyanate therein in an amount of 0.1 g/m² or more. In impregnating the adhesive with an iso-thiocyanate, the iso-thiocyanate may be mixed with a solvent or fatty oil having a good compatibility with the adhesive, and the adhesive may be then impregnated with the resulting mixture. The method for impregnating the adhesive with the iso-thiocyanate is not limited and may be a gravure coating and a Mayer bar-coating, as well as a spray coating, a curtain coating, a stripe coating from a nozzle, an immersion, etc. It is preferable that the impregnating process is carried out at a temperature of an atmosphere including the adhesive layer in a range of room temperature or less.

To produce the above-described biocidal self-adhesive, an adhesive promptly soluble in or swellable by an iso-thiocyanate because of its compatibility with the latter is applied to a gas-barrier film capable of being a barrier to the iso-thiocyanate, such as an aluminum-coated polyethylene terephthalate film, thereby forming an adhesive layer, and impregnating the adhesive layer with the iso-thiocyanate. This process ensures that an amount of iso-thiocyanate which is not available in the prior art process can be supported effectively. It should be noted that the gradual releasing of the iso-thiocyanate can be controlled by laminating a film such as polyethylene and polypropylene films having a permeability to the iso-thiocyanate, to a surface of the adhesive layer. In addition, the iso-thiocyanate can be held for a long period of time by laminating a gas-barrier film to the surface of the adhesive layer.

The self-adhesive article is basically of such a configuration that the biocidal self-adhesive is applied to at least one surface of a base material, including the above-described configuration. More specifically, the self-adhesive article comprises a biocidal self-adhesive supplied to the whole or a portion of one surface or opposite surfaces of a base material such as a resinous film made of a polyethylene terephthalate, a polypropylene, a polyvinyl chloride, a polyethylene, a polycarbonate, a polyvinylidene chloride, a polyacrylonitrile, an ethylene-vinyl alcohol copolymer, etc.; a paper; a fabric; a synthetic paper; a metal foil or the like. Usually, a film treated with a release agent and having a gas-barrier property is preliminarily temporarily laminated to the self-adhesive article in order to protect the adhesive layer. Such a self-adhesive article is referred to as an adhesive label or an adhesive sheet. It will be understood that the article of the present invention includes the form of a so-called adhesive tape made by applying an adhesive layer to one surface of a base material, while treating the other surface with a release agent, and rolling the resulting material.

It is as described above that the gradual releasing can be controlled by changing the gas-barrier property of the base material. It is optional that a deposited or coated layer may be provided on the base material, if required.

With the biocidal self-adhesive and the self-adhesive article impregnated with the iso-thiocyanate to hold the latter therein according to the present invention, the bacteriostatic, bactericidal, fungicidal, microbiocidal and freshness-maintaining effects possessed by the iso-thiocyanate can be widely utilized in a variety of fields, because the iso-thiocyanate can be held in the adhesive at a high concentration and effectively, but also it is possible to utilize the releasing of the vapor of the iso-thiocyanate without need for a special apparatus by profitably using an advantage of the adhesive that the article can be bonded to all materials. In addition, the use of the process comprising the steps of forming the adhesive layer and then impregnating the adhesive layer with the iso-thiocyanate ensures that the iso-thiocyanate can be held in the adhesive layer at a far higher concentration, as compared with a process comprising the steps of preliminarily incorporating an iso-thiocyanate into an adhesive and then forming an adhesive layer.

The present inventors have repeated zealous studies for an application of the above-described self-adhesive article and as a result, it has been found that the above-described problems are overcome by a combination of an iso-thiocyanate-impermeable barrier sheet and/or an iso-thiocyanate permeation controlling sheet with a self-adhesive impregnated with an iso-thiocyanate to hold the latter therein, or an iso-thiocyanate-containing layer formed from a paper or a non-woven fabric impregnated with an iso-thiocyanate to hold the latter therein through the medium of a low volatility oily liquid.

More specifically, an iso-thiocyanate gradually-releasing sheet according to the present invention comprises an iso-thiocyanate supporting layer which is covered, on its opposite sides, with an iso-thiocyanate-impermeable barrier sheet and/or an iso-thiocyanate permeation controlling sheet.

In this case, when one side of the layer is covered with the barrier sheet and the other side is covered with the controlling sheet, or when both the sides are covered with the controlling sheet, the gradual releasing of the iso-thiocyanate is controlled by the controlling sheet. When both the sides are covered with the barrier sheet, the gradual releasing of the iso-thiocyanate is controlled by the exposed area of the end face of the iso-thiocyanate supporting layer.

The iso-thiocyanate supporting layer is formed by impregnating an adhesive with the iso-thiocyanate to hold the latter therein, or by impregnating a support such as a paper and a non-woven fabric with the iso-thiocyanate to hold the latter therein through the medium of a low volatility oily liquid or the like.

In impregnating the adhesive with the iso-thiocyanate to hold the latter therein, the adhesive promptly soluble in or swellable by the iso-thiocyanate because of its compatibility with the iso-thiocyanate is applied to the gas-barrier film such as an aluminum-coated polyethylene terephthalate serving as a barrier to the iso-thiocyanate, thereby forming an adhesive layer, which is then impregnated with the iso-thiocyanate, and a film permeable to the iso-thiocyanate, such as a polyethylene film, a polypropylene film, an extremely thin polyethylene terephthalate film, is laminated to adhesive layer, thereby forming an iso-thiocyanate gradually-releasing sheet. This process ensures that an amount of the iso-thiocyanate which is incapable of being supported in the prior art can be supported effectively.

When the paper or the non-woven fabric is impregnated with the iso-thiocyanate to hold the latter therein through the medium of a low volatility oily liquid or the like, the low volatility oily liquid such as a polybutene containing the iso-thiocyanate dissolved therein is applied to a non-laminated surface of a paper or a non-woven fabric laminated, on its side, by an adhesive or by coextrusion, with a gas-barrier film serving as a barrier to the iso-thiocyanate, such as an aluminum-coated polyethylene terephthalate film, and such surface is further laminated with a film permeable to the iso-thiocyanate, such as a polyethylene film formed through an adhesive applying treatment, thereby forming an iso-thiocyanate gradually-releasing sheet. This process ensures that an amount of the iso-thiocyanate which is incapable of being supported in the prior art can be supported effectively.

Examples of the low volatility oily liquids are a polybutene, acrylic and methacrylic resins having a lower molecular weight, an epoxy resin, mineral oils, animal and vegetable oils such as olive, soybean and bovine oils, liquid paraffin, etc., but any liquids other than those described herein by way of example can be used, if they have a compatibility with the iso-thiocyanates, cannot react with the iso-thiocyanates and have a fluidity at ambient temperature.

When the iso-thiocyanate supporting layer is formed of an adhesive, it is desirable that the iso-thiocyanate is held in the adhesive by impregnation at a concentration in a range of 0.1 to 50% by weight based on the adhesive. Even if the iso-thiocyanate supporting layer is formed of either an adhesive or the paper or the non-woven fabric, it is desirable that the iso-thiocyanate is held in the adhesive or the paper or the non-woven fabric by impregnation at an amount of 0.1 g/m$^2$ or more.

However, the amount of the iso-thiocyanate is selected depending upon individual uses and hence, may be out of the above-described range in some cases.

Examples of the iso-thiocyanate-impermeable barrier sheets employed in the present invention include resinous films such as polyvinylidene chloride, polyacrylonitrile, ethylene-vinyl alcohol copolymer, polyethylene terephthalate and polycarbonate films; metal foils and the like. Examples of the iso-thiocyanate permeation controlling sheets include resinous films such as polyethylene, polypropylene and polyvinyl chloride films, papers, fabrics and synthetic papers. Even with the barrier sheet, the permeability thereof can be varied by reducing the thickness of a film and thus, such a barrier sheet can be also used as a controlling sheet.

The iso-thiocyanate-impermeable barrier sheet and the iso-thiocyanate-permeation controlling sheet may be used as a single layer structure or as a different sheet-laminated structure.

The iso-thiocyanates and the adhesives soluble in or swellable by the iso-thiocyanates which can be used are those described above for the adhesive article.

The iso-thiocyanate gradually-releasing sheet according to the present invention is capable of holding the iso-thiocyanate therein at a high concentration and effectively by the above-described configuration, but also capable of controlling the releasing of the vapor of the iso-thiocyanate by selection of the film.

Further, the present inventors have repeated zealous studies for another application of the above-described adhesive article and as a result, have overcome the problems in the prior art freshness maintaining means by utilizing the above-described knowledge that by using, as an adhesive, a polymer soluble in or swellable by an isothiocyanate, the iso-thiocyanate can be held in the polymer by impregnation, with physical properties of the adhesive being maintained.

More specifically, a self-adhesive sheet according to the present invention for sterilizing a material to be packed and maintaining the freshness of the material comprises an adhesive layer 2 impregnated with an iso-thiocyanate to hold the latter therein and mounted on a base sheet 1 having a low permeability to the iso-thiocyanate, as compared with a packing material for a material to be packed, as shown in FIG. 1.

In the self-adhesive sheet shown in FIG. 1, used as a base sheet 1 was a sheet which includes an aluminum-coated film 1b on one side of a polyethylene terephthalate (PET) film 1a and which has little permeability to iso-thiocyanates. In FIG. 1, reference numeral 3 designates an iso-thiocyanate-barrier release sheet including a silicone-treated release layer 3b on one side of a PET film 3a.

The self-adhesive sheet for sterilizing a material to be packed and maintaining the freshness of the material is selected depending upon the relative relationship with a packing material, but it is preferable that a base material having a total iso-thiocyanate-barrier property is used. Such materials include polymers such as a polyethylene terephthalate, a polycarbonate, a polyvinylidene chloride, a polyacrylonitrile and an ethylene-vinyl alcohol copolymer, and metal foils.

With the above-described sterilizing and freshness-maintaining self-adhesive sheet, the types of the adhesive and the iso-thiocyanate, the amount and method of impregnation of the iso-thiocyanate in adhesive and the self-adhesive sheet producing process are the same as those described above for the self-adhesive article and hence, the description thereof is not repeated here.

A method for sterilizing and freshness-maintaining a material to be packed according to the present invention comprises affixing a self-adhesive sheet of the type described above to an outer surface of a packing material for a material to be packed.

Thus, it is possible to sterilize the material to be packed and to maintain the freshness of such material, without destruction of the packing material. The packing material is not limited in any way, and any compositions can be used, if they have a lower barrier effect to iso-thiocyanates than that of the self-adhesive base material.

The extremely appropriate sterilization and freshness-maintaining can be performed by selecting the size of the self-adhesive sheet, the affixing place, the affixing time and the amount of iso-thiocyanate held by impregnation.

According to the present invention, the freshness-maintaining bactericidal and fungicidal effects and the like for food products can be widely utilized, because the above-described means makes it possible to release the vapor of the iso-thiocyanate through the packing material to the content in the packing material such as food products without need for a special apparatus by profitably using an advantage of the adhesive that the article and sheet can be bonded to all materials.

THE BEST MODE FOR CARRYING OUT THE INVENTION

Figure 1:
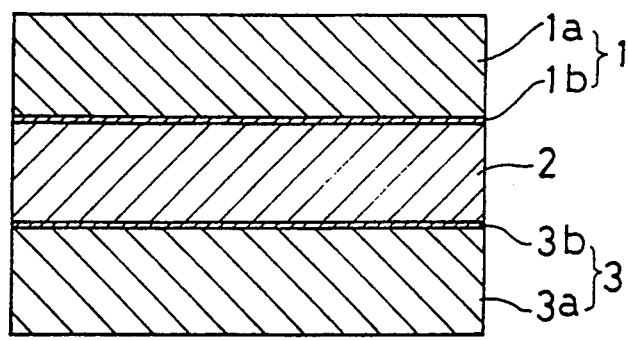
FIG. 1 is a diagram illustrating a biocidal self-adhesive sheet for sterilizing a material to be packed and maintaining the freshness of the material according to the present invention.

The present invention will now be described in detail by way of particular examples, but is not limited to these examples in any way.

EXAMPLE 1

There was prepared an ethyl acetate solution containing 40% by weight of a copolymer formed of 97% by weight of 2-ethylhexyl acrylate and 3% by weight of acrylic acid. An isocyanate-based cross-linking agent was added in an amount of 1% by weight to the solution, and the mixture was applied onto an aluminum-coated polyester film. The resulting material was dried for 2 minutes at 100° C., thus producing an self-adhesive sheet with its adhesive layer having a thickness of 30 µm. Further, the adhesive layer was impregnated with a stock solution of an allyl iso-thiocyanate at room temperature, thereby preparing a self-adhesive sheet containing 10% by weight of the allyl iso-thiocyanate in the adhesive. An aluminum-coated polyester film treated on one side with a silicone was laminated to the self-adhesive sheet to provide a self-adhesive article having a release film thereon.

EXAMPLE 2

A self-adhesive article having a release film thereon was produced in the same manner as in Example 1, except that 0.1% by weight of the allyl iso-thiocyanate was contained in the adhesive.

EXAMPLE 3

A self-adhesive article having a release film thereon was produced in the same manner as in Example 1, except that 25% by weight of the allyl iso-thiocyanate was contained in the adhesive.

EXAMPLE 4

A self-adhesive article having a release film thereon was produced in the same manner as in Example 1, except that 50% by weight of the allyl iso-thiocyanate was contained in the adhesive.

EXAMPLE 5

Dissolved in toluene were 100 parts of a styrene-isoprene-styrene block copolymer (Califlex TR1107 made by Shell Chemistry Corp.), 60 parts of liquid paraffin and 150 parts of a tackifier (Alcon P100 made by Arakawa Chemistry K.K.). The resulting solution was applied to an aluminum-coated polyester film, and dried for 2 minutes at 100° C., thereby producing a self-adhesive sheet with its adhesive layer having a thickness of 30 µm. Further, the adhesive layer was impregnated with a stock solution of an allyl iso-thiocyanate at room temperature, thereby preparing a self-adhesive sheet containing 5% by weight of the allyl iso-thiocyanate. An aluminum-coated polyester film treated on one side with a silicone was laminated to the self-adhesive sheet to provide a self-adhesive article having a release film thereon.

EXAMPLE 6

A solution of 2-ethylhexyl-acrylate acrylic acid copolymer in ethyl acetate, prepared in the same manner as in Example 1, was applied onto a release surface of an aluminum-coated polyester film having one side treated with a release agent, and was then dried for 2 minutes at 100° C. thereby producing a self-adhesive sheet with its adhesive layer having a thickness of 25 µm. This sheet was laminated to a non-woven fabric. Further, an adhesive layer having a thickness of 25 µm was separately formed on a release surface of an aluminum-coated polyester film treated on one side with a release agent, and was impregnated with an allyl iso-thiocyanate at room temperature. The non-woven fabric side of the self-adhesive sheet/non-woven fabric laminate and the adhesive side of the self-adhesive sheet impregnated with the allyl iso-thiocyanate were laminated to each other, thereby providing a double-sided self-adhesive article containing 10% by weight of the allyl iso-thiocyanate.

Comparative Example 1

Using a silicone adhesive, an adhesive layer of 30 µm was formed on an aluminum-coated polyester film,, and a stock solution of an allyl iso-thiocyanate was applied to the adhesive layer to provide a self-adhesive sheet. This sheet is laminated to an aluminum-coated film treated on one side with a fluorine-based release agent, thereby providing a self-adhesive article having a release film laminated to the aluminum-coated film.

Comparative Example 2

A double sided self-adhesive article was produced in the same manner as in Example 6, except that the adhesive layer was impregnated with no allyl iso-thiocyanate.

Then, the adhesion (according to JIS Z0237) was measured for the self-adhesive articles produced in Examples 1 to 5 and Comparative Example 1, thereby providing results as given in Table 1 below.

TABLE 1

|  | Adhesion (g/25 mm, against SUS) |
| --- | --- |
| Example | |
| 1 | 900 |
| 2 | 1,200 |
| 3 | 650 |
| 4 | 160 |
| 5 | 1,350 |
| Comparative Example | |
| 1 | 0 |

As apparent from Table 1, it can be seen that each of the self-adhesive articles produced in Examples 1 to 5 has an adhesion property, even if the allyl iso-thiocyanate is contained therein at a high concentration, and this enables the formation of a sheet from these articles, the affixing thereof to an object and the lamination thereof. In contrast, it can be seen that when the silicone adhesive insoluble in or unswellable by the allyl iso-thiocyanate is used as the adhesive, the resulting article has no adhesion property, because the allyl iso-thiocyanate remains as liquid on the surface of the adhesive and the surface of the release film.

The % residue of the allyl iso-thiocyanate, when the self-adhesive article having the release film and produced in Example 1 was left to stand at room temperature, was measured to provide results as given in Table 2.

TABLE 2

| | Residue Lapse of time (day) | | | |
| --- | --- | --- | --- | --- |
| Example | after 1 day | after 3 days | after 7 days | after 15 days |
| 1 | 99.3 | 99.0 | 98.2 | 96.7 |

As apparent from Table 2, it can be seen that even if the self-adhesive article is left to stand at room temperature, the volatilization of the allyl iso-thiocyanate can be reduced to the minimum by the fact that the self-adhesive article assumes the form as in Example 1.

Then, using the double-sided self-adhesive articles produced in Example 6 and Comparative Example 2, two veneers each having a thickness of 5 mm were laminated thereto. The resulting laminates were left to stand in a 70% Rh atmosphere at 25° C., and the propagation of fungi thereon was observed with the lapse of time. As a result, when the double sided self-adhesive article produced in Example 6 was used, little generation of fungi was observed even after one month, whereas when the double sided self-adhesive article produced in Comparative Example 2 was used, fungi were generated on a portion of the laminate after one week, and the fungi were spread over substantially the entire surface of the laminate after two weeks.

Figure 2:
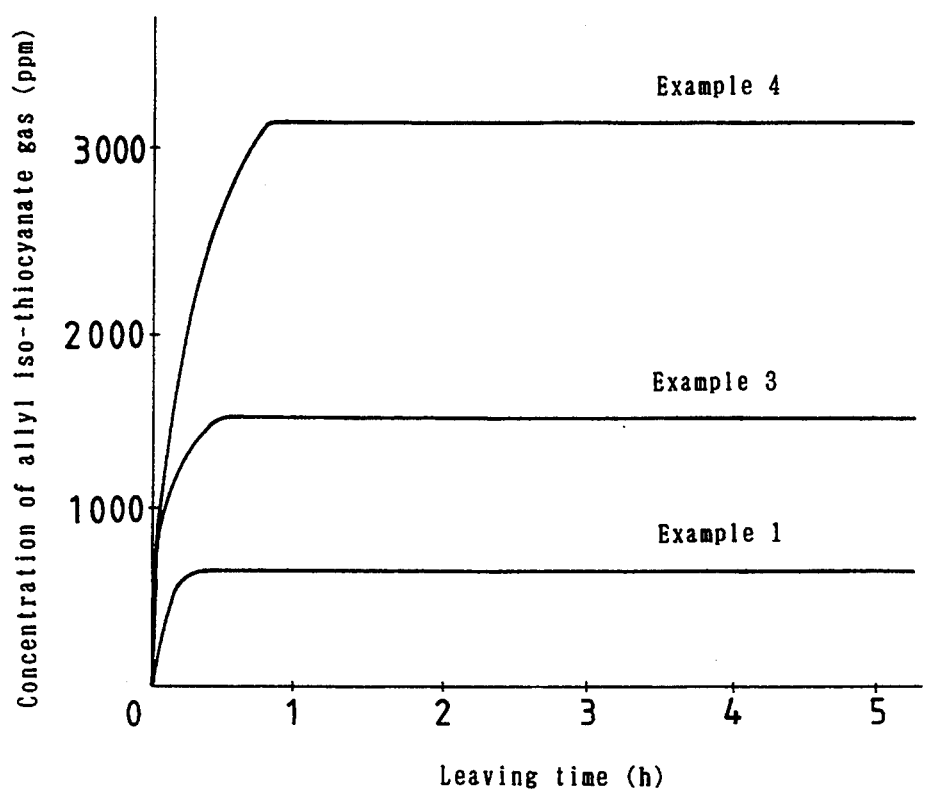
FIG. 2 is a graph illustrating the iso-thiocyanate releasing characteristic of a biocidal self-adhesive according to the present invention.

Then, the release film of each of the self-adhesive articles having the release film and produced in Examples 1, 3 and 4 was peeled off and left to stand in a 500 cm$^3$ stainless container, so that the adhesive surface cannot come into contact with an inner wall of the container. The concentration of the allyl iso-thiocyanate in the container was measured with the lapse of time by a gas chromatography. The result showed that each of the self-adhesive articles released the allyl iso-thiocyanate rapidly, so that the concentration of the allyl iso-thiocyanate in the sealed container was kept constant, as shown in FIG. 2.

EXAMPLE 7

There was prepared an ethyl acetate solution containing 40% by weight of a copolymer formed of 97% by weight of 2-ethylhexyl acrylate and 3% by weight of acrylic acid. An iso-cyanate-based cross-linking agent was added in an mount of 1% by weight to the solution. The resulting mixture was applied to a polyester film having a thickness of 3 μm and dried for one minute at 100° C. to form an adhesive layer of 30 μm. Then, an allyl iso-thiocyanate was applied to the adhesive layer in a room temperature condition by a gravure coating (using a gravure mesh: Lattice 120 Mesh made by Asahi Roll, Corp.), so that the allyl iso-thiocyanate was contained in the adhesive layer. The resulting film was laminated to a polyethylene film having a thickness of 50 μm to produce an allyl iso-thiocyanate containing sheet.

EXAMPLE 8

An acrylic adhesive layer of 30 μm was formed on a polyester film having a thickness of 38 μm in the same manner as in Example 7. Then, using a Mayer bar, the adhesive surface was coated with an allyl iso-thiocyanate, so that the allyl iso-thiocyanate was contained in the adhesive layer. The resulting film was laminated to a polyester film treated with a release agent and having a thickness of 38 μm to provide a self-adhesive sheet containing the allyl iso-thiocyanate.

Comparative Example 3

An iso-cyanate-based cross-linking agent was added in an amount of 1% by weight to an ethyl acetate solution containing 40% by weight of a copolymer formed of 97% by weight of 2-ethylhexyl acrylate and 3% by weight of acrylic acid, and an allyl iso-thiocyanate was added to the solution in an amount of 20 parts by weight per 100 parts of the solution. The resulting mixture was applied to a polyester film having a thickness of 38 μm and dried for 1 minute at 80° C. to form an adhesive layer of 30 μm. The resulting film was laminated to a polyethylene film having a thickness of 50 μm to provide an allyl iso-thiocyanate containing sheet.

Comparative Example 4

Added to an emulsion solution containing 65% by weight of a copolymer formed of 97% by weight of 2-ethylhexyl acrylate and 3% by weight of acrylic acid was an allyl iso-thiocyanate in an amount of 32.5 parts by weight per 100 parts by weight of the solution. The resulting mixture was applied to a polyester film having a thickness of 38 μm and dried for 1 minute at 80° C. to form an adhesive layer of 30 μm. The resulting film was laminated to a polyester film treated with a release agent and having a thickness of 38 μm to provide an allyl iso-thiocyanate containing sheet.

Then, the content of each of the allyl iso-thiocyanates in Examples 7 and 8 and Comparative Examples 3 and 4 was measured to provide results as given in Table 3.

The content was determined by cutting a sample sheet into a piece having a size of 20 cm×10 cm, leaving the cut piece to stand in an atmosphere at 40° C. under 10 Torr for 48 hours using a vacuum drier, removing the allyl iso-thiocyanate, and finding the content from the resulting variation in weight and the amount of adhesive applied.

TABLE 3

| Example | Content of allyl iso-thiocyanate (%) |
|---|---|
| 7 | 19.19 |
| 8 | 28.26 |
| Comparative Example | |
| 3 | 0.11 |
| 4 | 0.23 |

EXAMPLE 9

Figure 3:
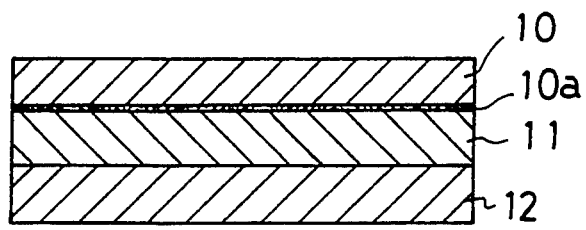
FIG. 3 is a diagram illustrating one embodiment of an iso-thiocyanate gradually-releasing sheet according to the present invention.

An acrylic adhesive layer 11 containing 20% by weight of an allyl iso-thiocyanate was formed on a deposited surface 10a of an aluminum-coated polyethylene terephthalate film 10 having a thickness of 25 μm, as shown in FIG. 3. The resulting film and a polyethylene film 12 having a thickness of 60 μm were laminated to each other to provide a gradually releasing sheet.

The releasing of the allyl iso-thiocyanate was examined, and the result showed that the releasing was sustained for about one hour at a release rate of 10.6 g/m$^2$.hr.

EXAMPLE 10

A gradually releasing sheet was produced in the same manner as in Example 9, except that the polyethylene in Example 9 was replaced by a polyethylene terephthalate film having a thickness of 16 μm.

The releasing of the allyl iso-thiocyanate was examined, and the result showed that the releasing was sustained for about 36 hours at a release rate of 0.28 g/m$^2$.hr.

EXAMPLE 11

A gradually releasing sheet was produced in the same manner as in Example 9, except that the polyethylene in Example 9 was replaced by a polyethylene terephthalate film having a thickness of 50 μm.

The releasing of the allyl iso-thiocyanate was examined, and the result showed that the releasing was sustained for about 105 hours at a release rate of 0.09 g/m$^2$.hr.

EXAMPLE 12

A gradually releasing sheet was produced in the same manner as in Example 9, except that the polyethylene in Example 9 was replaced by a polypropylene film having a thickness of 60 μm.

The releasing of the allyl iso-thiocyanate was examined, and the result showed that the releasing was sustained for about 12 hours at a release rate of 0.83 g/m$^2$.hr.

EXAMPLE 13

A gradually releasing sheet was produced in the same manner as in Example 9, except that the polyethylene in Example 9 was replaced by an aluminum-deposited polyethylene terephthalate film having a thickness of 25 μm.

The releasing of the allyl iso-thiocyanate was examined, and the result showed that the releasing was sustained for about 2900 hours at a release rate of 0.003 g/m$^2$.hr.

EXAMPLE 14

Figure 4:
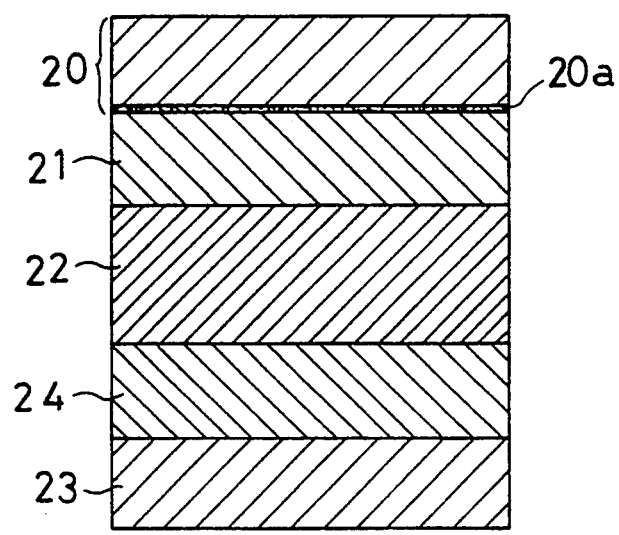
FIG. 4 is a diagram illustrating another embodiment of an iso-thiocyanate gradually-releasing sheet according to the present invention.

An acrylic adhesive layer 21 containing 20% by weight of an allyl iso-thiocyanate was formed on a coated surface 20a of an aluminum-coated polyethylene terephthalate film 20 having a thickness of 25 μm, as shown in FIG. 4. The film was laminated to a wood free paper 22 (Konywrap White 100 g/m$^2$ made by Lintec Corp.). The adhesive surface of a sheet comprising an acrylic adhesive layer 24 formed on a polyethylene film 23 having a thickness of 60 μm was laminated to the paper surface of the resulting laminate to provide a gradually releasing sheet having a nerve.

The releasing of the allyl iso-thiocyanate was examined, and the result showed that the releasing was sustained for about one hour at a release rate of 9.5 g/m$^2$.hr.

EXAMPLE 15

Figure 5:
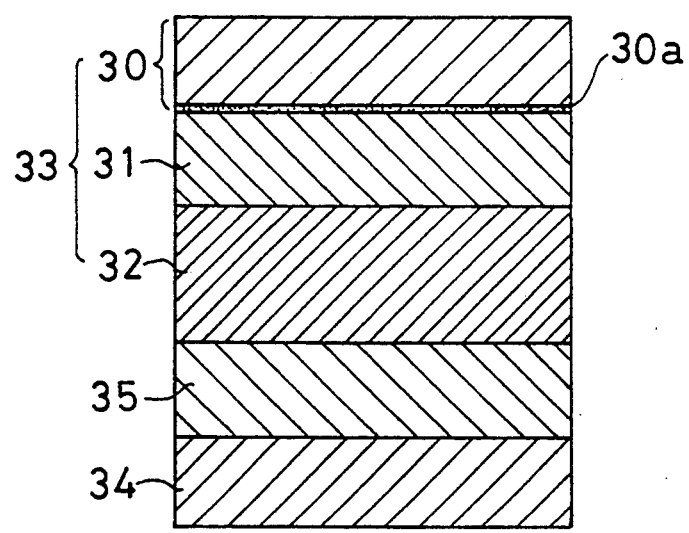
FIG. 5 is a diagram illustrating a further embodiment of an iso-thiocyanate gradually-releasing sheet according to the present invention.

An acrylic adhesive layer 31 was formed on a coated surface 30a of an aluminum-coated polyethylene terephthalate film 30 having a thickness of 25 μm, as shown in FIG. 5. The film was laminated to a paper 32 (Linter paper LCL-145 made by Taihei Paper Co., Ltd.) to prepare a laminate 33.

Then, an allyl iso-thiocyanate was dissolved in a polybutene (Nisseki Polybutene HV-100 made by Nippon Oil Co., Ltd.), so that the concentration of the allyl iso-thiocyanate was 5% by weight. This solution of allyl iso-thiocyanate in the polybutene was applied to the paper surface of the laminate 33, and then, an adhesive surface of a sheet having an acrylic adhesive layer 35 formed on a polyethylene terephthalate film 34 having a thickness of 25 μm was laminated to the coated surface of the laminate 33 to provide a gradually releasing sheet.

The releasing of the allyl iso-thiocyanate was examined, and the result showed that the releasing was sustained for about 60 hours at a release rate of 0.14 g/m$^2$.hr.

EXAMPLE 16

A self-adhesive sheet was produced, in accordance with the configuration shown in FIG. 1, by permitting an allyl iso-thiocyanate to be contained in an amount of 10% by weight in a self-adhesive article which was made by adding an iso-cyanate-based cross-linking agent in an amount of 1% by weight to a copolymer acrylic adhesive formed of 97% by weight of 2-ethylhexyl acrylate and 3% by weight of acrylic acid. A loaf of bread and boiled rice were placed into a polyethylene sack (20 mm×85 mm×0.08 mm) which was then sealed. Subsequently, the self-adhesive sheet was cut into a piece having a size of 2 cm×2 cm, and the release sheet was peeled off from the cut piece. The resulting sheet was affixed to the polyethylene sack from the outside. This sack was left to stand at room temperature. After two weeks, with regard to the loaf of bread, no variation was observed, and with regard to the boiled rice, a moisture condensation was only observed on an inner surface of the sack.

As a control, a loaf of bread and boiled rice were placed into a polyethylene sack which was then sealed, in the same manner as in Example 16. This sack was left to stand at room temperature without affixing of the self-adhesive sheet thereto. After about 5 days, fungi were developed on the loaf of bread, and after 10 days, these fungi were spread over substantially the entire surface of the loaf of bread. With regard to the boiled rice, on the other hand, fungi were developed thereon after 4 days, and the rice was rotted to have no trace of original form after 10 days.

EXAMPLE 17

A self-adhesive sheet similar to that in Example 16 was cut into a piece of 5 cm × 5 cm, and the release sheet was peeled off therefrom. Then, the cut piece was affixed to a central portion of an outer surface of a polyethylene package of each of three packs of boiled noodles. In addition, three packs of boiled noodles with no self-adhesive sheet affixed thereto were prepared as a control. The six packs in total were stored at room temperature, and after 7 days, variations in freshness thereof were compared.

The result of observation was as given in Table 4. A distinct freshness-maintaining effect due to the affixing of the allyl iso-thiocyanate containing self-adhesive sheet was observed, as given in Table 4.

TABLE 4

| | Result of observation | | | |
|---|---|---|---|---|
| | change of color | | Foul smell | |
| Sample | After 3 days | after 7 days | after 3 days | after 7 days |
| group with self-adhesive sheet affixed | 0/3 | 1/3* | 0/3 | 0/3 |
| Control group | 1/3 | 3/3 | 2/3 | 3/3 |

*change of color extremely in part

EXAMPLE 18

Twelve small rice cake packs each placed into a polyethylene sack were divided into four groups each comprising three rice cake packs. One group was used as a control (untreated), and with regard to the three other groups, an allyl iso-thiocyanate containing self-adhesive sheet similar to that in Example 16 was affixed to a central portion of a wrapping film of each group under conditions given in Table 5.

TABLE 5

| Test No. | Size of self-adhesive sheet (cm$^2$) |
|---|---|
| (1) | 3 |
| (2) | 5 |
| (3) | 7 |
| (4) | 0 (Control) |

Each sample was stored for long time at room temperature, and the test was carried out for the following items:

1) The condition of fungi developed: after 1 day, 3 days and 7 days from the affixing
2) The remaining odor of mustard: after 1 day and 7 days from the affixing The test results were as given in Table 6.

TABLE 6

| Test group No. | Appearance | | | Remaining mustard odor** | |
|---|---|---|---|---|---|
| | after 1 day | after 3 days | after 7 days | after 1 day | after 7 days |
| 1 | − | − | ± | ± | − |

TABLE 6-continued

| Test group No. | Appearance | | | Remaining mustard odor** | |
|---|---|---|---|---|---|
| | after 1 day | after 3 days | after 7 days | after 1 day | after 7 days |
| 2 | − | − | ± | + | − |
| 3 | − | − | − | + | − |
| 4 (control) | − | ± | + | | |

*Judgment of the appearance is as follows:
+Fungi were developed over substantially the entire region
±Fungi were developed in part
−There was no change
**Criterion of judgment is as follows:
+There was no odor of mustard
±There was a little odor of mustard
−There was no odor of mustard In the group with the allyl iso-thiocyanate containing self-adhesive sheet affixed, the development of fungi was inhibited in proportion to the size of the sheet. On the other hand, the odor of mustard was sensed in all of the groups (1) to (3) after 1 day, but was reduced after 7 days to such an extent that it could not be already sensed, which indicates the odor of this degree has little effect on the food taste.

Possibility of Industrial Application

With the biocidal self-adhesive and the process for producing the same according to the present invention, the iso-thiocyanate can be supported at a high concentration and moreover, the self-adhesive article can be properly affixed to a desired place in any form such as sheet, tape and label forms by utilization of the adhesion property of the adhesive, thereby effectively utilizing the bacteriostatic, bactericidal and microbiocidal properties of the iso-thiocyanate.

In the prior art methods for incorporating the iso-thiocyanate in clathration to a cyclodextrin and for adsorbing the iso-thiocyanate to a porous carrier such as a clay mineral, a slight amount of the iso-thiocyanate is merely contained in the final form of the sheet, but also the cost of the sheet is very high. In contrast, with the iso-thiocyanate gradually-releasing sheet of the present invention, a large amount of the iso-thiocyanate can be contained in the sheet and further, the gradual releasing of the iso-thiocyanate is possible. In addition, the cost can be minimized, leading to an inexpensive article.

In the case of the prior art vacuum pack and Ageless (Trademark), it is necessary to conduct the packing in the packing line together with the material to be packed, and sealability and air-tightness are required for packing. In contrast, with the self-adhesive sheet for sterilizing the material to be packed and for maintaining the freshness of the material to be packed according to the present invention, even if a small amount of the iso-thiocyanate is leaked, the iso-thiocyanate is replenished from the self-adhesive sheet. Therefore, the sterilizing and freshness-maintaining effects can be exhibited sufficiently, even if the air-tightness is small. Further, the time for affixing of the sheet need not necessarily be in the manufacture line, and even if the sheet is affixed after buying of a food product by a general purchaser, the same effect is obtained.

What is claimed is

1. An iso-thiocyanate gradually releasing sheet comprising:
   (a) an iso-thiocyanate supporting layer which comprises an adhesive impregnated with an iso-thiocyanate in an amount of 0.1 to 50% by weight of said adhesive;

(b) a barrier sheet covering one side of said iso-thiocyanate supporting layer, said barrier sheet being impermeable to iso-thiocyanate; and (c) an iso-thiocyanate permeation controlling sheet covering said iso-thiocyanate supporting layer on the side opposite to the side covered by the barrier sheet, said iso-thiocyanate permeation controlling sheet being permeable to the vapor of said iso-thiocyanate.

2. An iso-thiocyanate gradually releasing sheet as in claim 1, wherein said adhesive consists essentially of a polymer which is soluble in or swellable by said iso-thiocyanate.

3. An iso-thiocyanate gradually releasing sheet as in claim 2, wherein said polymer is a copolymer of a first monomer which is an alkyl acrylate or an alkyl methacrylate, wherein the alkyl group has at least 4 carbon atoms, and a second monomer which is copolymerizable with the first monomer.

4. An iso-thiocyanate gradually releasing sheet as in claim 1, wherein said barrier sheet is a laminate of at least two layers.

5. An iso-thiocyanate gradually releasing sheet as in claim 1, wherein said iso-thiocyanate permeation controlling sheet is a laminate of at least of two layers.

6. An iso-thiocyanate gradually releasing sheet comprising:

(a) an iso-thiocyanate supporting layer which comprises a paper or a non-woven fabric which is impregnated with an iso-thiocyanate in a medium of an oily liquid having low volatility, wherein the amount of iso-thiocyanate is at least 0.1 g/m$^2$;

(b) a barrier sheet covering one side of said iso-thiocyanate supporting layer, said barrier sheet being impermeable to iso-thiocyanate; and (c) an iso-thiocyanate permeation controlling sheet covering said iso-thiocyanate supporting layer on the side opposite to the side covered by the barrier sheet, said iso-thiocyanate permeation controlling agent being permeable to the vapor of said iso-thiocyanate.

7. An iso-thiocyanate gradually releasing sheet as in claim 6, wherein said barrier sheet is a laminate of at least two layers.

8. An iso-thiocyanate gradually releasing sheet as in claim 6, wherein said iso-thiocyanate permeation controlling sheet is a laminate of at least two layers.

9. An iso-thiocyanate gradually releasing sheet comprising:

(a) an iso-thiocyanate supporting layer which comprises an adhesive impregnated with an iso-thiocyanate in an amount of 0.1 to 50% by weight of said adhesive;

(b) a first barrier sheet covering one side of said iso-thiocyanate supporting layer, said barrier sheet being impermeable to said iso-thiocyanate; and (c) a second barrier sheet covering said iso-thiocyanate supporting layer on the side opposite to the side covered by the first barrier sheet.

10. An iso-thiocyanate gradually releasing sheet as in claim 9, wherein said adhesive consists essentially of a polymer which is soluble in or swellable by said iso-thiocyanate.

11. An iso-thiocyanate gradually releasing sheet as in claim 10, wherein said polymer is a copolymer of a first monomer which is an alkyl acrylate or an alkyl methacrylate, wherein the alkyl group has at least 4 carbon atoms, and a second monomer which is copolymerizable with the first monomer.

12. An iso-thiocyanate gradually releasing sheet as in claim 9, wherein said barrier sheet is a laminate of at least two layers.

13. An iso-thiocyanate gradually releasing sheet comprising:

(a) an iso-thiocyanate supporting layer which comprises a paper or a non-woven fabric which is impregnated with an iso-thiocyanate in a medium of an oily liquid having low volatility, wherein the amount of iso-thiocyanate is at least 0.1 g/m$^2$;

(b) a first barrier sheet covering one side of said iso-thiocyanate supporting layer, said barrier sheet being impermeable to said iso-thiocyanate; and (c) a second barrier sheet covering said iso-thiocyanate supporting layer on the side opposite to the side covered by the first barrier sheet.

14. An iso-thiocyanate gradually releasing sheet as in claim 13, wherein said barrier sheet is a laminate of at least two layers.

15. An iso-thiocyanate gradually releasing sheet comprising:

(a) an iso-thiocyanate supporting layer which comprises an adhesive impregnated with an iso-thiocyanate in an amount of 0.1 to 50% by weight of said adhesive;

(b) a first iso-thiocyanate permeation controlling sheet covering one side of said iso-thiocyanate supporting layer; and (c) a second iso-thiocyanate permeation controlling sheet covering said iso-thiocyanate supporting layer on the side opposite to the side covered by the first iso-thiocyanate permeation controlling sheet, wherein the first and second iso-thiocyanate permeation controlling sheets are permeable to the vapor of said iso-thiocyanate.

16. An iso-thiocyanate gradually releasing sheet as in claim 15, wherein said adhesive consists essentially of a polymer which is soluble in or swellable by said iso-thiocyanate.

17. An iso-thiocyanate gradually releasing sheet as in claim 16, wherein said polymer is a copolymer of a first monomer which is an alkyl acrylate or an alkyl methacrylate, wherein the alkyl group has at least 4 carbon atoms, and a second monomer which is copolymerizable with the first monomer.

18. An iso-thiocyanate gradually releasing sheet as in claim 15, wherein said iso-thiocyanate permeation controlling sheet is a laminate of at least two layers.

19. An iso-thiocyanate gradually releasing sheet comprising:

(a) an iso-thiocyanate supporting layer which comprises a paper or a non-woven fabric which is impregnated with an iso-thiocyanate in a medium of an oily liquid having low volatility, wherein the amount of iso-thiocyanate is at least 0.1 g/m$^2$;

(b) a first iso-thiocyanate permeation controlling sheet covering one side of said iso-thiocyanate supporting layer; and (c) a second iso-thiocyanate permeation controlling sheet covering said iso-thiocyanate supporting layer on the side opposite to the side covered by the first iso-thiocyanate permeation controlling sheet, wherein the first and second iso-thiocyanate permeation controlling sheets are permeable to the vapor of said iso-thiocyanate.

20. An iso-thiocyanate gradually releasing sheet as in claim 19, wherein said iso-thiocyanate permeation controlling sheet is a laminate of at least two layers.

* * * * *